US007345066B2

United States Patent
Auguet et al.

(10) Patent No.: US 7,345,066 B2
(45) Date of Patent: Mar. 18, 2008

(54) USE OF THIAZOLE DERIVATIVES FOR PREPARING A MEDICINE FOR PROTECTING MITOCHONDRIA

(75) Inventors: Michel Auguet, Palaiseau (FR); Pierre-Etienne Chabrier de Lassauniere, Paris (FR); Jeremiah Harnett, Gif-sur-Yvette (FR)

(73) Assignee: Societe de Conseils de Recherches et d'Applications Scientifiques (S.C.R.A.S.), Paris (FR)

( * ) Notice: Subject to any disclaimer, the term of this patent is extended or adjusted under 35 U.S.C. 154(b) by 666 days.

(21) Appl. No.: 10/483,823

(22) PCT Filed: Jul. 25, 2002

(86) PCT No.: PCT/FR02/02660

§ 371 (c)(1),
(2), (4) Date: Jan. 13, 2004

(87) PCT Pub. No.: WO03/009843

PCT Pub. Date: Feb. 6, 2003

(65) Prior Publication Data

US 2004/0248885 A1 Dec. 9, 2004

(30) Foreign Application Priority Data

Jul. 26, 2001 (FR) .................... 01 09979

(51) Int. Cl.
*A01N 43/78* (2006.01)
(52) U.S. Cl. ...................... 514/365; 514/838
(58) Field of Classification Search ................ 514/220
See application file for complete search history.

(56) References Cited

U.S. PATENT DOCUMENTS

| 4,914,207 | A | * | 4/1990 | Nagel et al. ................. 546/167 |
| 5,364,862 | A | | 11/1994 | Spada et al. |
| 6,262,069 | B1 | | 7/2001 | Liebeschuetz et al. |

FOREIGN PATENT DOCUMENTS

| EP | 0397365 | 11/1990 |
| FR | 2764889 | 12/1998 |
| FR | 28006155 | 5/2001 |
| WO | 0054729 | 9/2000 |
| WO | 0076971 | 12/2000 |
| WO | 0126656 | 4/2001 |

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*

Wyatt et al, "Structure-activity . . . Antagonist", Bioorganic & Medicinal Chemistry Letters (2001), 11(10), 1301-1305, XP001066283.

* cited by examiner

*Primary Examiner*—Michael G. Hartley
*Assistant Examiner*—GiGi Huang
(74) *Attorney, Agent, or Firm*—Charles A. Muserlian

(57) ABSTRACT

The invention concerns compounds of general formula (I), wherein: A represents one of the radicals in which $R^5$ represents independently a hydrogen atom, or alkyl; $R^6$, $R^7$ and $R^8$ independently represent a hydrogen atom, alkyl, cycloalkyl, hydroxy or alkoxy; $R^{11}$ represents a hydrogen atom of alkyl; and $R^9$, $R^{10}$ and $R^{12}$ independently represent a hydrogen atom, alkyl, hydroxy or alkoxy; B represents a hydrogen atom or alkyl; n represents an integer from 0 to 5; $R^1$ and $R^2$ independently represent a hydrogen atom, alkyl or cycloalkyl; $R^3$ and $R^4$ independently represent a hydrogen atom or an alkyl radical, or $R^3$ and $R^4$ together form with the nitrogen atom which bears them a heterocycle optionally substituted comprising in all 1 to 2 heteroatoms and 5 to 7 members. Said compounds can be used for preparing a medicine for protecting mitochondria, and in particular a medicine for preventing or treating cirrhosis.

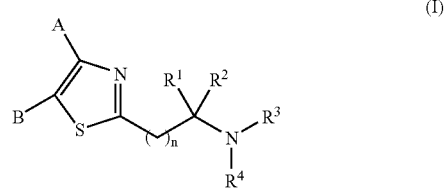

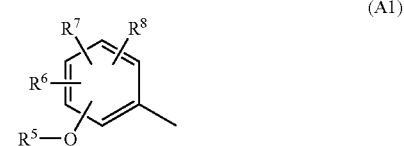

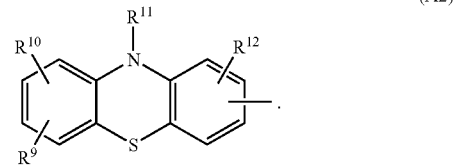

1 Claim, No Drawings

USE OF THIAZOLE DERIVATIVES FOR PREPARING A MEDICINE FOR PROTECTING MITOCHONDRIA

This application is a 371 of PCT/FR02/02660 filed Jul. 25, 2002.

A subject of the present invention is the use of the thiazole derivatives of general formula (I) described below for preparing a medicament intended to protect the mitochondria, and in particular a medicament intended to prevent or treat cirrhosis of the liver.

The Applicant has already described in PCT Patent Application WO 01/26656 thiazole, oxazole and imidazole derivatives inhibiting lipidic peroxidation and/or monoamine oxidases and/or modulating the sodium channels. These properties give these compounds useful therapeutic applications such as, in particular, the treatment of neurodegenerative diseases or pain.

The Applicant has just now discovered in a surprising manner that certain specific compounds among those described in PCT Patent Application WO 01/26656 moreover have the ability to protect the mitochondria, which opens up new therapeutic applications such as for example the prevention or treatment of cirrhosis of the liver.

In fact, these compounds oppose the swelling of mitochondria when it is induced by agents capable of causing the mitochondrial membrane potential to drop. It is now well established that swelling of the mitochondria is caused by a modification of the permeability of the internal membrane of the mitochondria to small molecules with a molecular weight greater than 1500 daltons. This phenomena called permeability transition following a fall in the membrane potential is associated with the irreversible opening of a high conductance pore, osmotic swelling of the matrix and a release of mitochondrial factors with the ability to trigger the initial stages of apoptosis (cytochrome c, apoptosis inducing factor): see Gunter, T. E. and Pfeiffer, D. R., Mechanisms by which mitochondria transport calcium, *Am. J. Physiol.* (1990), 258, C755-C786; Hunter, D. R. and Haword, R. A., The $Ca^{2+}$-induced membrane transition in mitochondria. III. Transitional $Ca^{2+}$ release, *Arch. Biochem. Biophys.* (1979), 195, 468-477; Bratton, S. B. and Cohen, G. M., Apoptotic death sensor: an organelle's alter ego, *TRENDS* (2001), 22, 306-315).

It then becomes particularly useful to find compounds which would prevent or reduce the swelling of mitochondria by opposing the opening of this high conductance pore. This property which can be demonstrated on isolated mitochondria can bring clinical benefits in therapeutic indications different from those described in PCT Patent Application WO 01/26656, which consist of mitochondrial functional or genetic disorders.

The relationship between the swelling of mitochondria and certain pathologies is in particular described in the following references:

for mitochondrial diseases of genetic origin: Clostre, Mitochondries: "découvertes physiopathologiques récentes et nouvelles perspectives thérapeutiques", *Ann. Pharm. Fr.* (2001), 59, 3-21;

for sepsis (septic shock): Fink, Cytopathic hypoxia. Mitochondrial dysfunction as a mechanism contributing to organ dysfunction in sepsis, *Crit. Care Clin.* (2001), 17, 219-237;

for cirrhosis of the liver: Tsukamoto et al., Current concept in the pathogenesis of alcoholic liver injury, *FASEB J* (2001), 15(8):1335-49;

for cardiac, renal or hepatic toxicity induced by medicamentous agents: Lewis et al., Mitochondrial toxicity of antiviral drugs, *Nat. Med.*, 1(5), 417-22.

The fact that the compounds of general formula (I) described below prevent the swelling of mitochondria therefore allows their use to be envisaged in particular for preparing a medicament intended to treat a disease/a disorder chosen from the following diseases/disorders: myopathies, amyopathies, ptosis, optical atrophy, pigmentary retinopathy, deafness, hepatomegalia, hepatic cytolysis, hypertrophic cardiomyopathy, chronic progressive external ophthalmoplegia, Kearns-Sayre syndrome, Leigh's syndrome, Leber's syndrome, NARP syndrome, MELAS syndromes, Pearson's syndrome, sepsis, cirrhosis of the liver, and cardiac, renal or hepatic toxicity induced by medicamentous agents.

Preferably, the compounds of general formula (I) described below are used for preparing a medicament intended to treat a disease/a disorder chosen from the following diseases/disorders: amyopathies, ptosis, optical atrophy, pigmentary retinopthy, deafness, hepatic cytolysis, chronic progressive external ophthalmoplegia, Kearns-Sayre syndrome, Leigh's syndrome, Leber's syndrome, NARP syndrome, MELAS syndromes, Pearson's syndrome, sepsis, cirrhosis of the liver, and cardiac, renal or hepatic toxicity induced by medicamentous agents.

More preferentially, the compounds of general formula (I) described below are used for preparing a medicament intended to treat a disease/a disorder chosen from the following diseases/disorders: amyopathies, ptosis, optical atrophy, pigmentary retinopathy, deafness, hepatic cytolysis, chronic progressive external ophthalmoplegia, Kearns-Sayre syndrome, Leigh's syndrome, Leber's syndrome, NARP syndrome, MELAS syndromes, Pearson's syndrome, cirrhosis of the liver, and cardiac, renal or hepatic toxicity induced by medicamentous agents.

Quite particularly, the compounds of general formula (I) described below are used for preparing a medicament intended to treat cirrhosis of the liver.

According to the invention, the compounds of general formula (I)

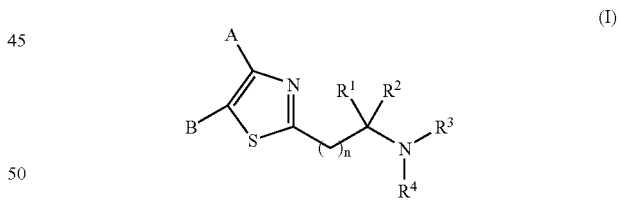

in which
A represents an (A1) radical

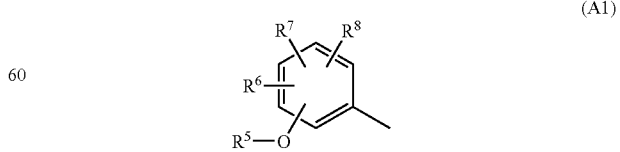

in which $R^5$ represents a hydrogen atom or an alkyl radical, $R^6$ represents a hydrogen atom or an alkyl, cycloalkyl, hydroxy or alkoxy radical, $R^7$ represents a hydrogen atom or an alkyl, cycloalkyl, hydroxy or alkoxy radical and $R^8$ represents a hydrogen atom or an alkyl, cycloalkyl, hydroxy or alkoxy radical, or also A represents an (A2) radical

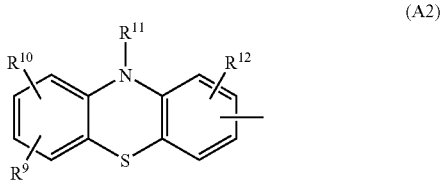

(A2)

in which $R^9$ and $R^{10}$ represent independently a hydrogen atom or a hydroxy, alkyl or alkoxy radical, $R^{11}$ represents a hydrogen atom or an alkyl radical and $R^{12}$ represents a hydrogen atom or a hydroxy, alkyl or alkoxy radical;

B represents a hydrogen atom or an alkyl radical;

n represents an integer from 0 to 5;

$R^1$ and $R^2$ represent independently a hydrogen atom or an alkyl or cycloalkyl radical;

$R^3$ and $R^4$ represent independently a hydrogen atom or an alkyl radical, or $R^3$ and $R^4$ form together with the nitrogen atom which carries them a heterocycle containing in total 1 to 2 heteroatoms and 5 to 7 members, the missing members of which heterocycle are chosen from —$CHR^{13}$—, —$NR^{14}$—, —O— and —S—, $R^{13}$ representing a hydrogen atom, the —OH group or an alkyl or alkoxy radical and $R^{14}$ representing a hydrogen atom or an alkyl, —$COR^{15}$, —$COOR^{15}$ or —$CONR^{16}R^{17}$ radical, $R^{15}$ representing an alkyl radical and $R^{16}$ and $R^{17}$ represent independently a hydrogen atom or an alkyl radical;

or the pharmaceutically acceptable salts of the compounds of general formula (I)

can be used for preparing a medicament intended to protect the mitochondria.

By alkyl or alkoxy, unless specified otherwise, is meant a linear or branched alkyl or alkoxy radical containing 1 to 6 carbon atoms. By cycloalkyl, unless specified otherwise, is meant a monocyclic carbon system containing 3 to 7 carbon atoms. Finally, by halogen, is meant the fluorine, chlorine, bromine or iodine atoms.

In addition, unless specified otherwise, by an optionally substituted radical is meant a radical containing one or more substituents chosen independently from the group containing a halogen atom and alkyl and alkoxy radicals.

By heterocycle, is meant in particular the piperidine, piperazine, morpholine and thiomorpholine radicals. By linear or branched alkyl having 1 to 6 carbon atoms, is meant in particular the methyl, ethyl, propyl, isopropyl, butyl, isobutyl, dry-butyl and tert-butyl, pentyl, neopentyl, isopentyl, hexyl, isohexyl radicals.

By pharmaceutically acceptable salt, is meant in particular addition salts of inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. The salts formed from bases such as sodium or potassium hydroxide are also within the scope of the present invention, when they can be used. For other examples of pharmaceutically acceptable salts, reference can be made to "Salt selection for basic drugs", *Int. J. Pharm.* (1986), 33, 201-217.

Moreover, certain compounds of general formula (I) can be presented in the form of enantiomers. The present invention includes the two enantiomeric forms and all combinations of these forms, including the "R,S" racemic mixtures. In an effort to simplify matters, when no specific configuration is indicated in the structural formulae, it should be understood that the two enantiomeric forms and their mixtures are represented.

Preferably, the compounds of the invention are such that they comprised at least one of the following characteristics:

A representing an (A1) radical

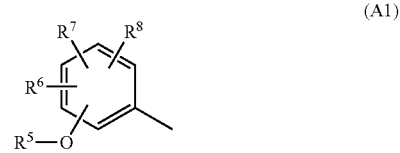

(A1)

in which $R^5$ represents a hydrogen atom or a methyl radical, $R^6$ represents a hydrogen atom or an alkyl, cycloalkyl, hydroxy or alkoxy radical, $R^7$ represents a hydrogen atom or an alkyl, cycloalkyl, hydroxy or alkoxy radical and $R^8$ represents a hydrogen atom or an alkyl, cycloalkyl, hydroxy or alkoxy radical, or also A representing an (A2) radical

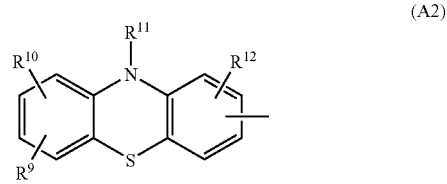

(A2)

in which $R^9$ and $R^{10}$ represent independently a hydrogen atom or a hydroxy, alkyl or alkoxy radical, $R^{11}$ represents a hydrogen atom or a methyl radical and $R^{12}$ represents a hydrogen atom or a hydroxy, alkyl or alkoxy radical;

B representing a hydrogen atom or a methyl or ethyl group;

n representing an integer from 0 to 3;

$R^1$ and $R^2$ representing independently a hydrogen atom or an alkyl radical;

$R^3$ and $R^4$ representing independently a hydrogen atom or an alkyl radical, or $R^3$ and $R^4$ forming together with the nitrogen atom which carries them a heterocycle containing in total 1 to 2 heteroatoms and 5 to 7 members, the missing members of which heterocycle are chosen from —$CHR^{13}$—, —$NR^{14}$—, —O— and —S—, $R^{13}$ representing a hydrogen atom, the —OH group or a methyl or methoxy radical and $R^{14}$ representing a hydrogen atom or an alkyl, —$COR^{15}$, —$COOR^{15}$ or —$CONR^{16}R^{17}$ radical, $R^{15}$ representing an alkyl radical and $R^{16}$ and $R^{17}$ represent independently a hydrogen atom or an alkyl radical.

More preferentially, the compounds of the invention are such that they comprised at least one of the following characteristics:

A representing an (A1) radical

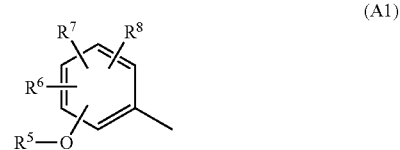

(A1)

in which $R^5$ represents a hydrogen atom, $R^6$ represents a hydrogen atom or an alkyl, cycloalkyl, hydroxy or alkoxy radical, $R^7$ represents a hydrogen atom or an alkyl, cycloalkyl, hydroxy or alkoxy radical and $R^8$ represents a hydrogen atom or an alkyl, cycloalkyl, hydroxy or alkoxy radical, or also A representing an (A2) radical

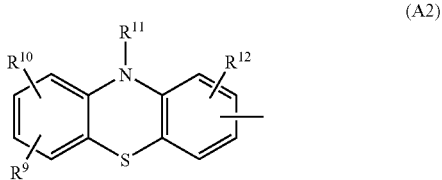

(A2)

in which $R^9$ and $R^{10}$ represent independently a hydrogen atom or a hydroxy, alkyl or alkoxy radical, $R^{11}$ represents a hydrogen atom and $R^{12}$ represents a hydrogen atom or a hydroxy, alkyl or alkoxy radical;

B representing a hydrogen atom or a methyl group;

n representing an integer from 0 to 2;

one of $R^1$ and $R^2$ representing a hydrogen atom, the other representing a hydrogen atom or an alkyl or cycloalkyl radical;

$R^3$ and $R^4$ representing independently a hydrogen atom or an alkyl radical, or $R^3$ and $R^4$ forming together with the nitrogen atom which carries them a heterocycle with 6 members containing in total 1 to 2 heteroatoms, the missing members of which heterocycle are chosen from —$CHR^{13}$—, —$NR^{14}$—, —O— and —S—, $R^{13}$ representing a hydrogen atom, the —OH group or a methyl radical and $R^{14}$ representing a hydrogen atom or an alkyl radical.

Yet more preferentially, the compounds of the invention are such that they comprised at least one of the following characteristics:

A representing an (A1) radical

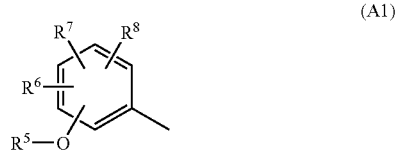

(A1)

in which $R^5$ represents a hydrogen atom, $R^6$ represents a hydrogen atom or an alkyl, hydroxy or alkoxy radical, $R^7$ represents a hydrogen atom or an alkyl, hydroxy or alkoxy radical and $R^8$ represents a hydrogen atom or an alkyl, hydroxy or alkoxy radical, or also A representing an (A2) radical

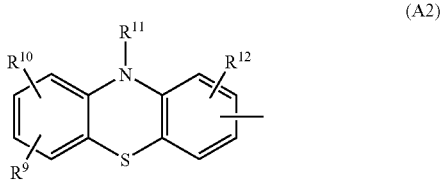

(A2)

in which $R^9$ and $R^{10}$ represent independently a hydrogen atom or a hydroxy, methyl, ethyl, methoxy or ethoxy radical, $R^{11}$ represents a hydrogen atom and $R^{12}$ represents a hydrogen atom or a hydroxy, methyl, ethyl, methoxy or ethoxy radical;

B representing a hydrogen atom;

n representing an integer from 0 to 1;

one of $R^1$ and $R^2$ representing a hydrogen atom, the other representing a hydrogen atom or an alkyl radical (and preferably a linear or branched alkyl radical containing 1 to 3 carbon atoms, in particular a methyl or ethyl radical);

one $R^3$ and $R^4$ representing independently a hydrogen atom or an alkyl radical, or $R^3$ and $R^4$ forming together with the nitrogen atom which carries them a heterocycle of 6 members containing in total 1 to 2 heteroatoms, the missing members of which heterocycle are chosen from —$CHR^{13}$—, —$NR^{14}$—, —O— and —S—, $R^{13}$ representing a hydrogen atom, the —OH group or a methyl radical and $R^{14}$ representing a hydrogen atom or an alkyl radical.

Particularly preferably, the (A1) radical is a radical

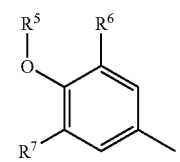

in which $R^5$ represents a hydrogen atom or an alkyl radical (and in particular a hydrogen atom), $R^6$ represents an alkyl radical (in particular the iso-propyl or tert-butyl radical and more particularly the tert-butyl radical) and $R^7$ represents an alkyl radical (in particular the iso-propyl or tert-butyl radical and more particularly the tert-butyl radical).

Also particularly preferred, the (A2) radical is a radical

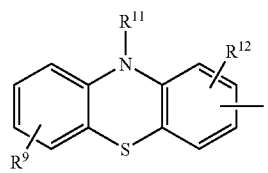

in which $R^9$ represents a hydrogen atom or a methyl or methoxy radical (and in particular a hydrogen atom), $R^{11}$ represents a hydrogen atom or a methyl radical (and in particular a hydrogen atom) and $R^{12}$ represents a hydrogen atom or a methyl or methoxy radical (and in particular a hydrogen atom)

Moreover:

cases where n represents 0 are more particularly preferred;

the variant of the invention according to which A represents an (A1) radical will generally be preferred over that according to which A represents an (A2) radical;

the case where $R^3$ or $R^4$ represent independently a hydrogen atom or an alkyl radical, is preferred to those in which $R^3$ or $R^4$ form together with the nitrogen atom which carried them a heterocycle;

when $R^3$ or $R^4$ represent an alkyl radical, it is preferably an alkyl radical containing 1 to 3 carbon atoms, and in particular a methyl or ethyl radical (quite particularly a methyl radical);

when $R^3$ and $R^4$ form together with the nitrogen atom which carries them a heterocycle, this heterocycle is preferably a piperazinyl, morpholinyl or thiomorpholinyl radical (and more preferentially a piperazinyl radical) or also a piperidinyl radical substituted (preferably in position 3 or 4) by a hydroxy radical;

when $R^6$, $R^7$ or $R^8$ represent an alkyl radical, it is preferably an alkyl radical containing 3 to 6 carbon atoms, and in particular a tert-butyl or iso-propyl radical.

In particular, the following compounds can be used according to the invention:

4-[3,5-bis(1,1-dimethylethyl)-4-hydroxyphenyl]-N-methyl-2-thiazolemethanamine;

N-methyl[4-(10H-phenothiazin-2-yl)-1,3-thiazol-2-yl]methanamine;

2,6-ditert-butyl-4-{2-[(4-methylpiperazin-1-yl)methyl]-1,3-thiazol-4-yl}phenol;

4-[2-(aminomethyl)-1,3-thiazol-4-yl]-2,6-di(tert-butyl)phenol;

2,6-ditert-butyl-4-{2-[1-(methylamino)ethyl]-1,3-thiazol-4-yl}phenol;

or their pharmaceutically acceptable salts.

The pharmaceutical compositions containing a compound of the invention can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form, for example, solutions, emulsions, suspensions or syrups. Appropriate liquid supports can be, for example, water, organic solvents such as glycerol or glycols, and as well as their mixtures, in varying proportions, in water.

The administration of a medicament according to the invention can be carried out by topical, oral, parenteral route, by intramuscular injection, etc.

The dose of a product according to the present invention, envisaged for the treatment of the diseases or illnesses mentioned above, varies according to the administration method, the age and the body weight of the subject to be treated as well as the subject's state, and it will be definitively decided by the attending doctor or veterinary surgeon. Such a quantity determined by the attending doctor or veterinary surgeon is called here "therapeutically effective quantity".

By way of illustration, the administration dose envisaged for a medicament according to the invention is comprised between 0.1 mg to 10 g according to the type of active compound used.

The preparation of the compounds of general formula (I) according to the present invention is described in PCT Patent Application WO 01/26656.

Unless defined differently, all the technical and scientific terms used here have the same meaning as that normally understood by an ordinary specialist in the field to which this invention belongs. Similarly, all the publications, patent applications, all the patents and all other references mentioned here are incorporated by way of reference.

The following examples are presented to illustrate the above procedures and should in no way be considered as a limit to the scope of the invention.

EXAMPLES

The following compounds:

4-[3,5-bis(1,1-dimethylethyl)-4-hydroxyphenyl]-N-methyl-2-thiazolemethanamine hydrochloride (compound 1), N-methyl[4-(10H-phenothiazin-2-yl)-1,3-thiazol-2-yl]methanamine hydrochloride (compound 2), 2,6-ditert-butyl-4-{2-[(4-methylpiperazin-1-yl)methyl]-1,3-thiazol-4-yl}phenol hydrochloride (compound 3), 4-[2-(aminomethyl)-1,3-thiazol-4-yl]-2,6-di(tert-butyl)phenol hydrochloride (compound 4) and 2,6-ditert-butyl-4-{2-[1-(methylamino)ethyl]-1,3-thiazol-4-yl}phenol hydrochloride (compound 5)

were subjected to the test which studies the swelling of isolated mitochondria of rat liver as described below.

All the compounds mentioned above were described in PCT Application WO 01/26656 or are accessible by synthesis methods similar to those described in this document.

Principle of the Test

The test consists of measuring the interaction of the compounds vis-to-vis the swelling of isolated mitochondria of rat liver, measured by spectrophotometric absorbance. The swelling of the isolated mitochondria of the liver is used as an indicator of the modification of permeability transition and can be induced by different agents: tert-butylhydroperoxide (t-BH); the methyl phenyl pyridinium ion ($MPP^+$) and potassium dihydrogen phosphate (Pi) in the presence of calcium ($Ca^{2+}$).

t-BH is metabolized by the glutathione peroxidase system, exhausting the reductive power of the mitochondria represented by NAD(P)H and glutathione (GSH) and leading to oxidation of the SH groups.

$MPP^+$ is an inhibitor of the I complex of the electron transport chain mitochondria causing a generation of free radicals, a reduction of the membrane potential facilitating the opening of the transition pore and the extrusion of cytochrome c.

The Pi triggers permeability transition by reducing the ADP concentration of the matrix, by stimulating lipidic peroxidation and the production of mitochondrial free radicals.

Preparation of the Mitochondria of Rat Liver

The liver from Sprague-Dawley rats weighing 240-260 g, fasted from the day before, (Charles River, France) is removed, weighed, sliced in 50 ml of extraction buffer (225 mM of mannitol; 75 mM of sucrose; 0.2 mM of EDTA; 5 mM of TRIS-HCl, pH 7.4 at 4° C.) and homogenized according to the protocol described by Johnson and Lardy (Isolation of liver and kidney mitochondria, *Methods Enzymol.* (1967), 10, 94-96) and Holtzman et al. (Effects of osmolar changes on isolated mitochondria of brain and liver, *J. Neurochem.* (1978), 30, 1409-1419) using a glass homogenizer (5 strokes). The homogenate is centrifuged for 5 minutes at 1,085 g. The resulting supernatant is centrifuged at 17,000 g for 10 minutes. Then the pellet is taken up in 12.5 ml of extraction buffer by gentle stirring using a glass rod, then the suspension is centrifuged at 17,000 g for 10 minutes. The pellet obtained is resuspended in suspension in 1 ml of extraction buffer at 4° C. The concentration of mitochondrial proteins (68.48±1.17 mg/ml) is determined by the Lowry method (Protein measurement with the folin phenol reagent, *J Biol. Chem*, 93, 1951: 265-275). The mitochondrial suspension is stored in ice and used within 3 hours.

Measurement of the Swelling of the Mitochondria of Rat Liver

Quantification of the swelling of the mitochondria is carried out by measurement with a spectrophotometer (Shimadzu UV-2401PC) light scatter at 540 nm. The mitochondria (final concentration of 0.5 mg proteins/ml for the induction of swelling by Pi or 1 mg/ml for t-BH and MPP+) are incubated in 3.6 ml of buffer containing:

when the inducer is t-BH: 225 mM mannitol, 75 mM sucrose, 3 mM HEPES, 5 mM succinate, and 0.5 nmoles rotenone/mg of proteins, pH 7.4, at 25° C.;

when the inducer is MPP+: 225 mM of mannitol, 75 mM sucrose, 5 mM HEPES, 5 mM/0.5 mM glutamate/malate, pH 7.4, at 25° C.;

when the inducer is Pi: 150 mM sucrose, 65 mM KCl, 2.5 mM succinate, 5 µM rotenone and 10 mM HEPES—KOH, pH 7.4, at 30° C.

A volume of 1.8 ml of the corresponding suspension is introduced into the measuring cuvette of the spectrophotometer as well as in the so-called reference cuvette in the presence of the compounds to be tested. Measurement of the absorbance variation ($\Delta A_{540}$) of the two cuvettes is carried out in parallel.

Induction of the Swelling of the Mitochondria of Rat Liver

When the inducer is t-BH: after incubation for 2 min at 25° C., 70 nmoles of $CaCl_2$ is added and 2 minutes later, 200 µM of t-BH is introduced into the measuring cuvette [modified Broekemeir and Pfeiffer method (Cyclosporin A is a potent inhibitor of the inner membrane permeability transition in liver mitochondria, J. Biol. Chem. (1989), 264, 7826-7830)].

When the inducer is MPP+: after incubation for 5 min at 25° C., 1 mM of MPP+ and 50 µM of $Ca^{2+}$ are introduced into the measuring cuvette followed 2 minutes later by 300 µM of Pi [modified method of Cassarino et al. (The parkinsonian neurotoxin MPP+ opens the mitochondrial permeability transition pore and releases cytochrome c in isolated mitochondria via an oxidative mechanism, Biochim. Biophys. Acta (1999), 1453, 49-62)].

When the inducer is Pi: after incubation for 1 min at 30° C., 10 µM of $CaCl_2$ is introduced into the two cuvettes. Five minutes later, the swelling is triggered by the introduction of 4 mM of potassium dihydrogen phosphate into the measuring cuvette only [modified method of Kowaltowski et al. (Effect of inorganic phosphate concentration on the nature of inner mitochondrial membrane alterations mediated by $Ca^{2+}$ ions. A proposed method for phosphate-stimulated lipid peroxidation, J. Biol. Chem. (1996), 271, 2929-2934) and Elimadi et al. (Trimetazidine counteracts the hepatic injury associated with ischemia-reperfusion by preserving mitochondrial function, J. Pharmacol. Exp. Ther. (1998), 286, 23-28)].

Analysis of the Data

The speed of absorbance reduction $A_{540}$ is proportional to the recruitment speed of the mitochondria in transitional permeability modification phase. This speed is expressed by the $\Delta A_{540}$/min/mg protein, calculated from the tangent of the steepest part of the absorbance as a function of time (UV-2101/3101PC Optional Kinetics Software). The effectiveness of the products, the effects of which are tested two to three times, is estimated by their ability to reduce in a significant manner the recruitment speed of the mitochondria in permeability modification phase. The comparisons are carried out using variance analysis. A value of $p<0.05$ is considered as statistically significant.

Results

Compounds 1 to 5 mentioned above have, at a concentration equal to or less than 25 µM, significantly reduced the recruitment speed of the mitochondria in permeability modification phase induced either by tBH, MPP+ or Pi.

The invention claimed is:

1. A method of treating cirrhosis of the liver in warm-blooded animals comprising administering to warm-blooded animals in need thereof an amount of a compound selected from the group consisting of -4-[3,5-bis(1,1-dimethylethyl)-4-hydroxyphenyl]-N-methyl-2-thiazolemethanamine hydrochloride, -4-[2-(aminomethyl)-1,3-thiazol-4-yl]-2,6-di(tert-butyl) phenol hydrochloride, -2,6-ditert-butyl-4-{2-[1-(methylamino)ethyl]-1,3-thiazol-4-yl}phenol hydrochloride and its pharmaceutically acceptable salts, sufficient to treat cirrhosis of the liver.

* * * * *